(12) United States Patent
Rauch

(10) Patent No.: US 7,785,282 B2
(45) Date of Patent: Aug. 31, 2010

(54) SPINAL ORTHOSIS

(76) Inventor: Isabelle E Rauch, 549 W. 23 St., #16B, New York, NY (US) 10027

(*) Notice: Subject to any disclaimer, the term of this patent is extended or adjusted under 35 U.S.C. 154(b) by 13 days.

(21) Appl. No.: 10/960,103

(22) Filed: Oct. 8, 2004

(65) Prior Publication Data

US 2006/0079821 A1   Apr. 13, 2006

(51) Int. Cl.
A61F 5/00 (2006.01)
A61F 5/37 (2006.01)
A61F 13/00 (2006.01)
A61B 19/00 (2006.01)

(52) U.S. Cl. .............. 602/19; 602/5; 128/846; 128/869; 128/873; 128/874

(58) Field of Classification Search ............... 602/16, 602/19–20, 32, 36, 5–6; 128/846, 869, 873, 128/874, 96.1, 870, 875
See application file for complete search history.

(56) References Cited

U.S. PATENT DOCUMENTS

| | | | | |
|---|---|---|---|---|
| 1,316,915 A * | 9/1919 | Meyer et al | ............ | 602/19 |
| 3,064,644 A * | 11/1962 | Patterson | ............ | 602/23 |
| 4,244,081 A * | 1/1981 | Beyer et al. | ............ | 16/228 |
| 4,829,989 A * | 5/1989 | Deamer et al. | ............ | 602/19 |
| 4,958,643 A * | 9/1990 | Pansiera | ............ | 602/16 |
| 5,176,622 A * | 1/1993 | Anderson et al. | ............ | 602/19 |
| 5,599,287 A * | 2/1997 | Beczak et al. | ............ | 602/19 |
| 5,728,172 A * | 3/1998 | Krieger | ............ | 623/44 |
| 5,876,361 A * | 3/1999 | Harris | ............ | 602/19 |
| 6,102,881 A * | 8/2000 | Quackenbush et al. | ........ | 602/28 |
| 6,171,272 B1 * | 1/2001 | Akita et al. | ............ | 602/28 |
| 6,190,343 B1 * | 2/2001 | Heinz et al. | ............ | 602/19 |
| 6,676,617 B1 * | 1/2004 | Miller | ............ | 602/5 |
| 6,752,774 B2 * | 6/2004 | Townsend et al. | ............ | 602/16 |
| 2003/0220594 A1 * | 11/2003 | Halvorson et al. | ............ | 602/19 |
| 2004/0220503 A1 * | 11/2004 | Kozersky | ............ | 602/19 |
| 2005/0137508 A1 * | 6/2005 | Miller | ............ | 602/19 |

OTHER PUBLICATIONS

Related co-pending U.S. Appl. No. 10/265,287.

* cited by examiner

Primary Examiner—Patricia M Bianco
Assistant Examiner—Brandon Jackson
(74) Attorney, Agent, or Firm—Miles & Stockbridge PC; James T. Carmichael; Patrick L. Miller

(57) ABSTRACT

A spinal orthosis comprising a torso unit, a base member secured to the torso unit, a spring biased hinge connected at a first end to the base member and connected at a second end to a sternal support, and one or more sternal pads (or plates) connected to the sternal support. The sternal pads (or plates) may be adapted to provide a posteriorly directed force based on a bias of the spring biased hinge. The spring biased hinge may include a receiving portion that can have an adjustment mechanism at a first end and a spring to provide bias for the spring biased hinge, wherein the adjustment mechanism can be moveable through the receiving portion so as to adjust the bias of the spring biased hinge.

25 Claims, 4 Drawing Sheets

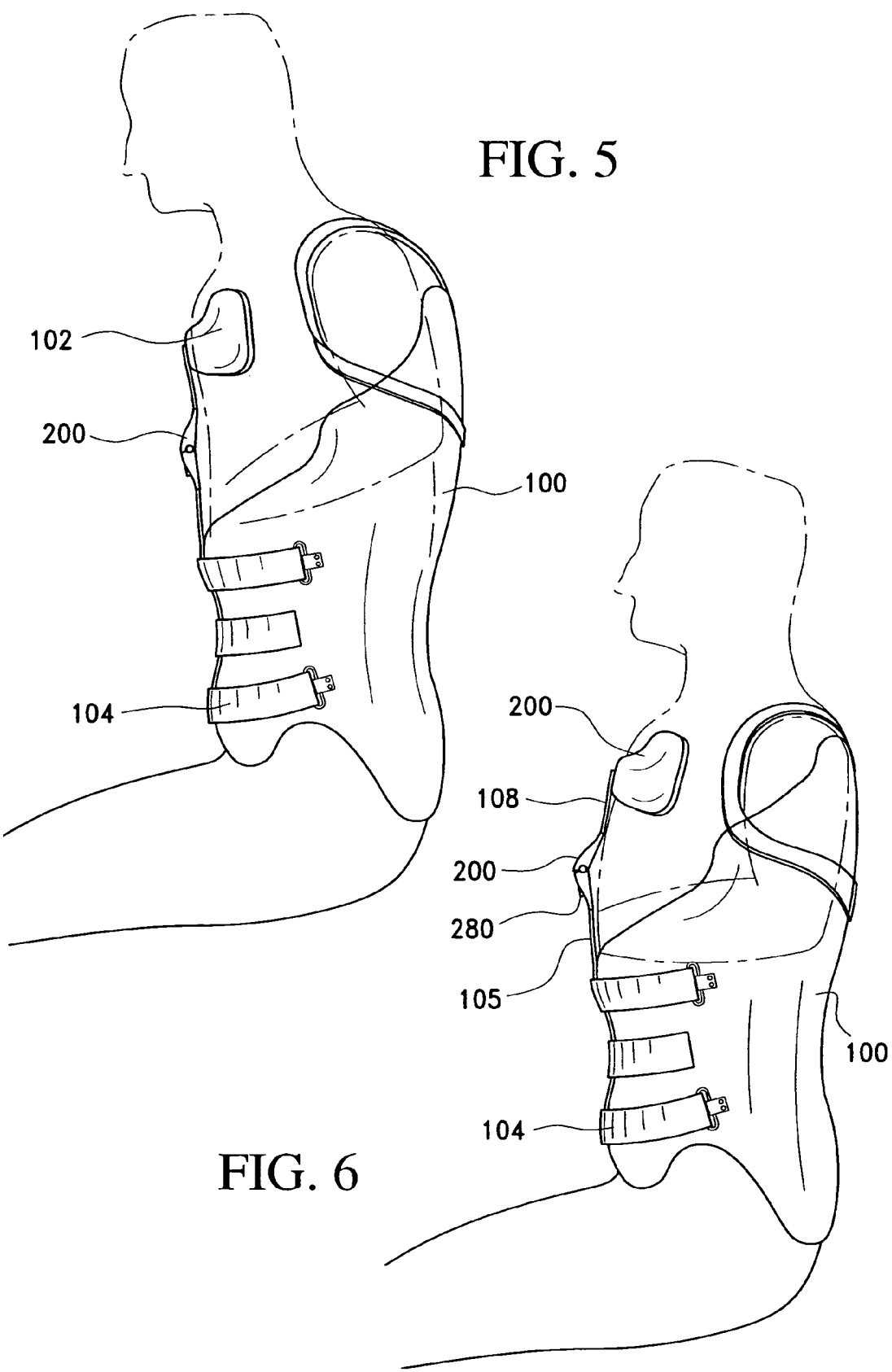

SPINAL ORTHOSIS

This application is related to U.S. patent application Ser. No. 10/265,287 entitled "Anterior Sternal Thoraco-Lumbosacral Spinal Orthosis," which is incorporated herein by reference in its entirety.

An exemplary aspect of this invention relates to spinal orthosis. More particularly, an exemplary aspect of the invention relates to spinal orthoses and a spring biased hinge mechanism that is capable of providing rigid frame spinal bracing for musculoskeletal injury, disease, or the like, that occurs, for example, in the thoracic, lumbar and sacral spinal regions.

The anatomy of the spine is usually divided into four major sections: the cervical, thoracic, the lumbar and the sacral. Each section is made up of individual bones called vertebrae with there being 7 cervical vertebrae, 12 thoracic vertebrae, and 5 lumbar vertebrae. In order to relieve pain that can sometimes be associated with back injuries, it may be necessary to temporarily hyperextend the spine by using some type of orthosis.

According to exemplary embodiments of the present invention, a spinal orthosis may comprise a torso unit, a base member secured to the torso unit, a spring biased hinge connected at a first end to the base member and connected at a second end to a sternal support, and one or more sternal pads (or plates) connected to the sternal support. In various embodiments, the spinal orthosis may be secured to a user such that the spring biased hinge is adjacent the user's chest and such that the sternal pad (or plate) is adjacent the user's sternal area.

The sternal pads may be adapted to provide a posteriorly directed force based on a bias of the spring biased hinge. The spring biased hinge may include at least a bump stop that limits the hinges range of movement and a receiving portion that includes first and second ends. The receiving portion may include an adjustment mechanism at the first end and a spring to provide bias for the spring biased hinge. The adjustment mechanism may be moveable through the receiving portion so as to adjust the bias of the spring biased hinge. More specifically, the adjustment mechanism can be moved toward the second end to increase the posteriorly directed force and moved away from the second end to decrease the posteriorly directed force.

According to exemplary embodiments of the present invention, a spinal orthosis features a semi-resilient material, such as either a homogenous material or a laminate, the laminate having at least one of a shell and a liner, the shell at least partially having at least one layer, for example, a clothing contact surface material, a core, a stiffener and, for example, a strengthening material. The liner can have at least one layer, for example, at least one of a resilient cushion and a dermal contact surface layer.

A second exemplary embodiment relates to a spinal orthosis featuring a semi-rigid semi-resilient material that can be, for example, a homogenous material or a laminate, with the laminate having at least one of a shell and a liner. The shell can, for example, at least partially have at least one layer of at least one of a clothing contact surface material, a core, a stiffener and a strengthening material. The liner can at least partially include at least one layer of at least of a one resilient cushion and a dermal contact surface layer.

A third exemplary embodiment includes a spring biased hinge attached to an anterior surface of the orthosis, the spring biased hinge biasing a sternal portion.

The clothing contact surface can be made of any one or more of a plastic, a metal, an alloy, a cloth, leather, a rubber, a polyethylene, a polypropylene, a polyvinylchloride, a polybuterate, a polystyrene, a polycarbonate, an aluminum, or the like.

The core can be, for example, made from one or more of a plastic, a metal, an alloy, a cloth, leather, a rubber, a polyethylene, a polypropylene, a polyvinylchloride, a polybuterate, a polystyrene, a polycarbonate, an aluminum, or the like.

The strengthening material can be made from one or more of a plastic, a metal, an alloy, carbon fibers, glass fibers, plastic fibers, a cloth, leather, a rubber, a polyethylene, a polypropylene, a polyvinylchloride, a polybuterate, a polystyrene, a polycarbonate, an aluminum, or the like.

The sternal pressure base, hinge and sternal pressure bar can be made from one or more of a plastic, a metal, an alloy, carbon fiber, fiberglass, an aluminum, or the like.

The stiffener can be, for example, made from one or more of a plastic, a metal, an alloy, a cloth, leather, a rubber, a polyethylene, a polypropylene, a polyvinylchloride, a polybuterate, a polystyrene, a polycarbonate, an aluminum, or the like.

The resilient cushion can be, for example, made from any one or more of a foam, a plastic foam, a cloth, leather, a rubber foam, a polyethylene foam, a polypropylene foam, a polyvinylchloride foam, a polybuterate foam, or the like.

The dermal contact surface can be made from any one or more of a plastic, a cloth, leather, a rubber, a polyethylene, a polypropylene, a polyvinylchloride, a polybuterate, a polystyrene, a polycarbonate, or the like, or some combination thereof.

An exemplary aspect of the invention features a spinal orthosis having an overlap to include at least one inner flap and at least one outer flap, with both the inner and the outer flaps extending in an essentially equivalent distance past a sagittal anterior-posterior midplane. A sternal pad assembly attaches to at least one of the outer flap and inner flap.

In accordance with another exemplary embodiment, a spinal orthosis features a chest module, such as a sternal plate, or a bridged pectoral pad set, wherein the chest module is at least partially supported by a hinge having an axis of motion perpendicular to a sagittal anterior-posterior midplane.

Another exemplary aspect of the invention relates to a spinal orthoses having a chest module being either a sternal plate or a bridged pectoral pad set. The chest module attaches via a hinge having an axis of motion perpendicular to the sagittal anterior-posterior midplane, collectively all the axes of motion defining a compound hinge, the compound hinge including a resilient element where the resilient element urges the at least one of the module attachment and the chest plate attachment in a posterior direction against a posterior pressure directing anchor point.

These and other aspects of the invention will be apparent from the following detailed discussion of the embodiments.

BRIEF DESCRIPTION OF THE DRAWINGS

FIG. 5 is an environmental view of the orthosis according to this invention; and FIG. 6 is a second environmental view of the orthosis according to this invention.

DETAILED DESCRIPTION

Figure 1:
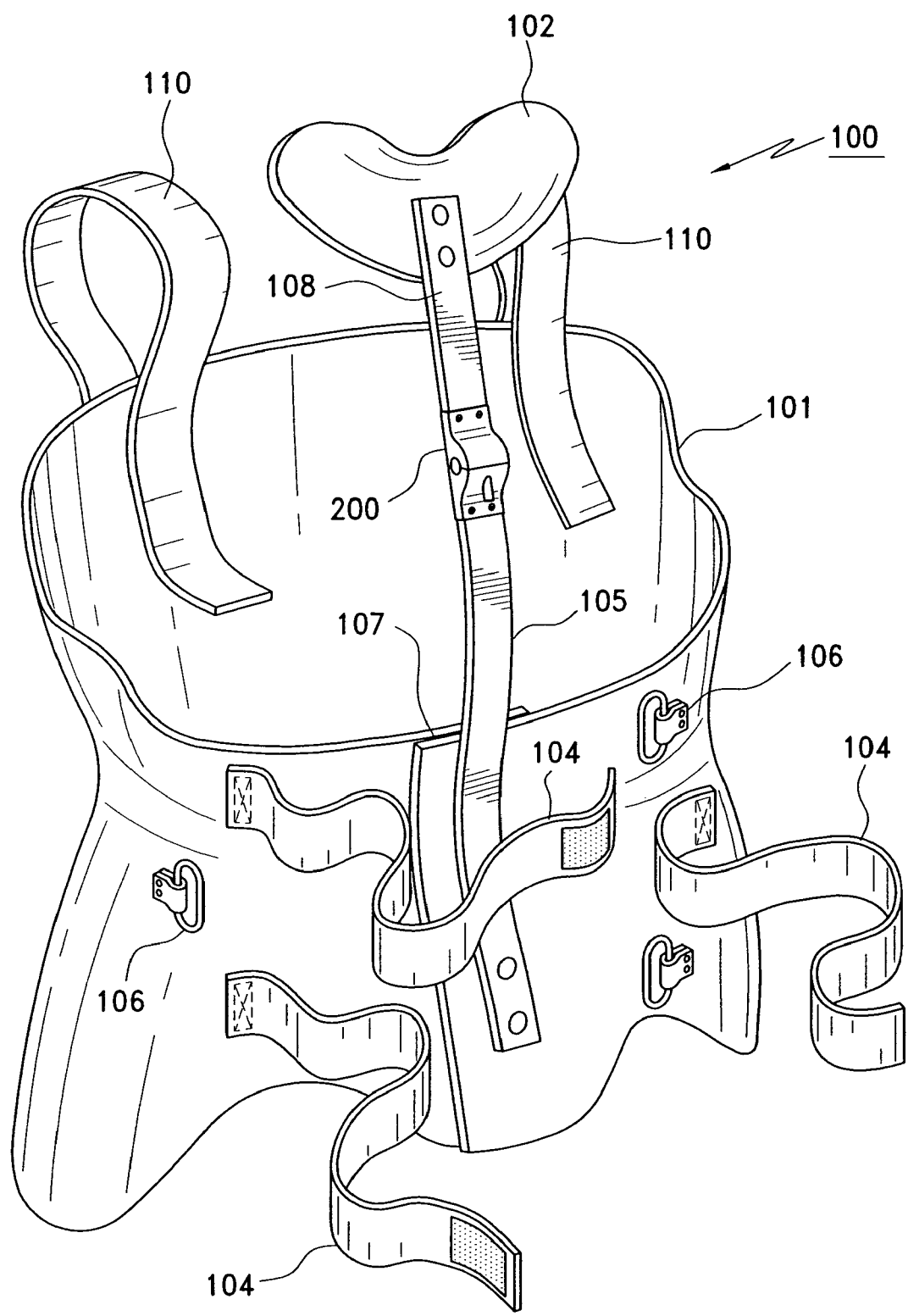
FIG. 1 is in perspective view illustrating an exemplary embodiment of the present invention.

FIG. 1 illustrates an exemplary embodiment of the orthosis module 100. The orthosis module 100 comprises a torso support portion 101, a sternal plate 102, a sternal pressure base 105, a spring biased hinge 200, a sternal pressure bar 108, one or more straps 110, and one or more adjustable straps 104 with corresponding strap loops 106.

While the torso support portion 101 of the orthosis module 100 that comes into contact and surrounds the torso of the patient as illustrated in FIG. 1 is shown as a substantially unitary structure, it should be appreciated that the torso support portion 101 could comprise multiple sections that are held together by a fastening system, or in general be of any shape or configuration that provides spinal orthosis.

For example, by utilizing the spring biased hinge, and adhering to basic biomechanical principles, the operation of the orthotic module can be expanded to any specific orthotic function. For example, use is not limited to spinal orthosis. The spring biased hinge and appropriate orthotic support could also be used in upper limb (hand wrist elbow, forearm) bracing and rehabilitation. For example, through the addition of uprights and cuffs with, for example, hook and loop closures, such as Velcro®, the spring biased hinge could be used to assist in reducing flexion or extension contractures at the elbow. The hinge can also be placed proximal to the volar surface, and by adding a distal opponens and a proximal forearm cuff, forces to resist palmarflexion or promote palmarflexion strengthening may be performed by patients.

The spring biased hinge and appropriate body brace could also be modified and placed anteriorly with a clip or clasp on one end and a calf cuff and upright on the other end of the hinge and be used in dorsiflexion and plantarflexion strengthening exercises. In general, the spring biased hinge and accompanying body braces/supports can be used in any application to include, for example, orthotic, orthopedic and rehabilitation of patients.

The exemplary orthosis module 100 in FIG. 1 wraps around a patient and forms an overlap 107 at an anterior face of the orthosis module 100. The orthosis module 100 can, for example as discussed above, be constructed of a semi-rigid contortable plastic material with, for example, a resilient lining. The overlap 107 in the orthosis module 100 allows adjustment to varying levels of tightness around the patient by the adjusting mechanism comprising the adjustable straps 104 and corresponding strap loops 106.

For example, the adjusting mechanism can comprise multiple adjustment straps 104 that attached to the orthosis module 100 on laterally opposite sides of the overlap 107 with one end of each adjustment strap 104 being affixed to the orthosis module 100 and on the other end threaded through a strap loop 106 and folded back onto itself and fixed, for example, through the use of a hook and loop fastening system. The adjustment straps 104 can, for example, alternate in different directions with one end of a first adjustment strap fixed to a first side of the orthosis module and the accompanying strap loop on the opposite side, with the next strap being fixed to the opposite side of the orthosis module 100, and the strap loop on the opposite side as illustrated in exemplary FIG. 1. The number of straps is not limited to three as illustrated, but rather can be varied, based on, for example, the size of the orthosis module, the amount of tightness required, and the like. Likewise, the adjusting mechanism need not be limited to straps and strap loops but could also be made from any one or more of laces, belts and buckles, and the like.

Furthermore, additional straps can be located on any portion of the orthosis module, such as straps 110, that can be further used to, for example, tighten a portion of the orthosis module 100, maintain the position of the orthosis module 100 on a patient, and the like. For example, as illustrated in FIG. 1, the straps 110 can be used in an over-the-shoulder type arrangement and fixed to the anterior face of the orthosis module by a fastening mechanism (not shown).

Also attached to the anterior face of the orthosis module 100 is a sternal pressure base 105 that is affixed, for example, to the anterior face of the orthosis module 100 where the overlap 107 occurs. The sternal pressure base 105 can be attached to the orthosis module 100 by many means including, but not limited to, bolts, screws, rivets, adhesives, clamps, molded interlocks, and the like. Furthermore, it should be appreciated that the sternal pressure base 105 could be integrally formed into the orthosis module 100 and can be fixed to or integrated into either the inner or outer flap.

The walls of the orthosis module 100 are contoured to exert compression from all sides by creating an increased hydraulic rigidity in a patient's abdominal section. This abdominal hydraulic rigidity increases the support between the pelvis and the thorax and provides corrective forces. The corrective forces are arranged in a 3-point pressure system, wherein the anterior portion of the orthosis module 100 provides a posteriorly directed force, the sternal plate 102 provides a second posteriorly directed force, and a posterior section of the orthosis module provides an anteriorly directed force.

Attached to the upper end of the sternal pressure base 105 is a spring biased hinge 200 which is also connected to the sternal plate 102. As described in greater detail hereinafter, the spring biased hinge 200 is capable of providing a posteriorly directed force due to the spring biased feature as discussed hereinafter. The spring biased hinge 200 is connected to the sternal pressure base 105 and sternal pressure bar 108 by, for example, bolts, screws, rivets, adhesives, clamps, molded interlocks, a friction fit, a mechanical fit, or any other fastening means and/or arrangement that is capable of holding the various components together.

While the exemplary embodiment illustrated in FIG. 1 shows the sternal plate 102 as a single component, such as a pad, it is to be appreciated in the sternal plate 102 can be configured, for example, in a wide variety of configurations including but not limited to a plurality of pads. Likewise the shape of the sternal plate(s) can be altered into any shape, including, but not limited to, a circle, oval, square, kidney-shape, or the like. Furthermore, the sternal plate 102 can include padding and is fixed to the external pressure bar by fastening means, such as those discussed in relation to the external pressure base.

Figure 2:
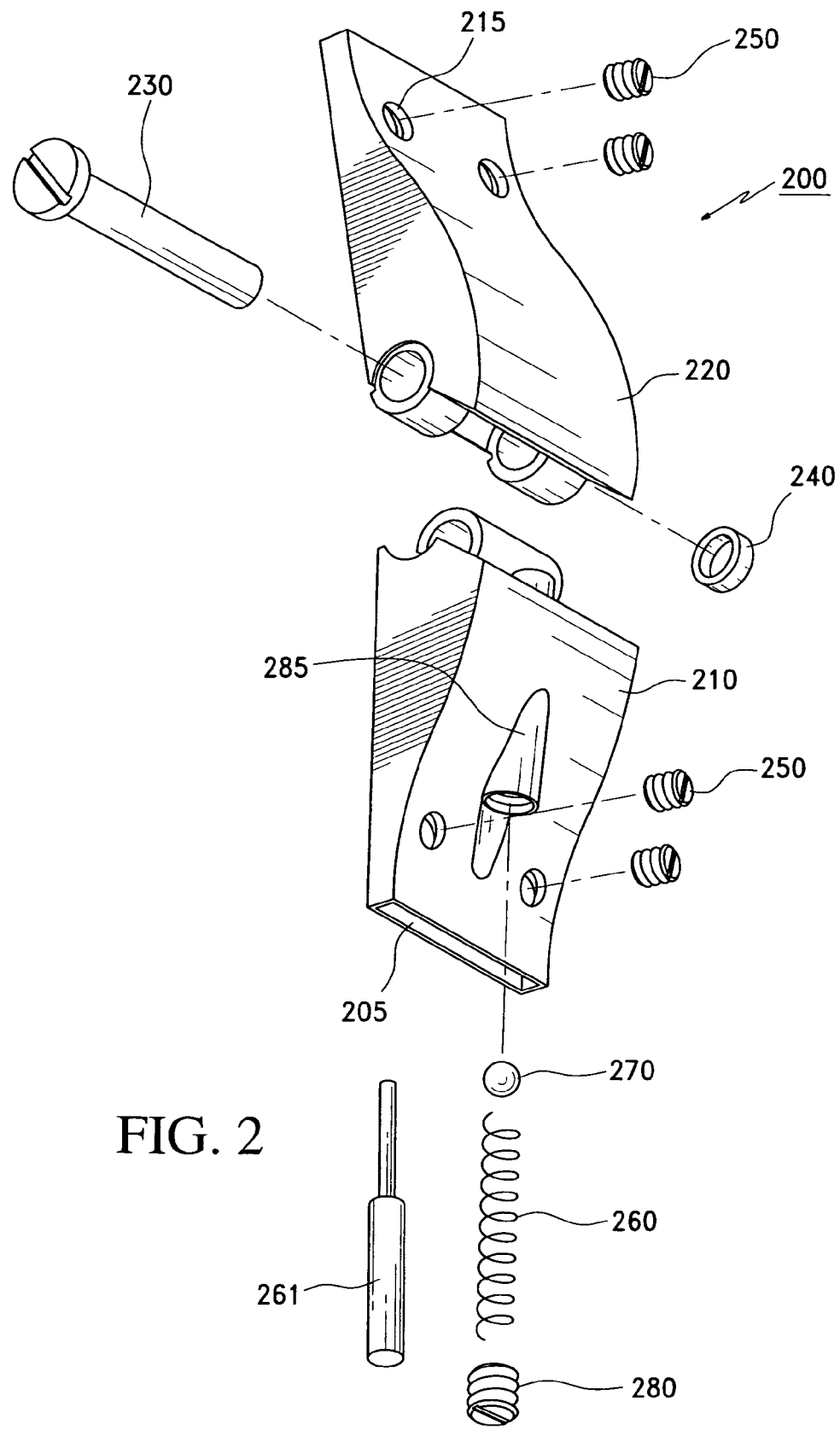
FIG. 2 is an exploded view of the spring biased hinge according to this invention.

FIG. 2 illustrates in greater detail an exploded view of the hinge 200. In particular, the exemplary spring biased hinge 200 comprises a sternal pressure base portion 210, a sternal pressure bar portion 220, a hinge pin 230, a nut 240, a plurality of, for example, set screws 250, a spring 260, a ball bearing 270, and a tension adjustment mechanism 280. As previously discussed, the sternal pressure base 105 can fit into slot 205 of the sternal pressure base portion 210 and secured, for example, by setscrews 250. In a similar manner, the sternal pressure bar 106 can be inserted into slot 215 and secured by setscrews 250. The spring biased hinge 200, and in particular the external pressure bar portion 220 and external pressure base portion 210 are hingedly connected by means of a hinge pin 230 which is secured by nut the 240. The spring biased hinged 200 is fixed to the external pressure base 105 in a manner such that the sternal plate 102 opens in a posteriorly directed manner. This spring biased hinge 200 when closed, allows the sternal plate 102 to be substantially parallel to the chest of the patient.

The tension adjusting mechanism 280, in cooperation with the spring 260 and ball bearing 270, provides a bias on the hinge which produces a posteriorly directed force that is applied by the sternal plate 102 to the chest of the patient. As, for example, the tension adjusting mechanism 280 is screwed into the corresponding threaded receiving portion 285, the spring 260 is placed under greater compressive force which presses the ball bearing 270 against a surface of the sternal pressure bar portion 220 thereby providing the posteriorly directed force.

Figures 3, 4:
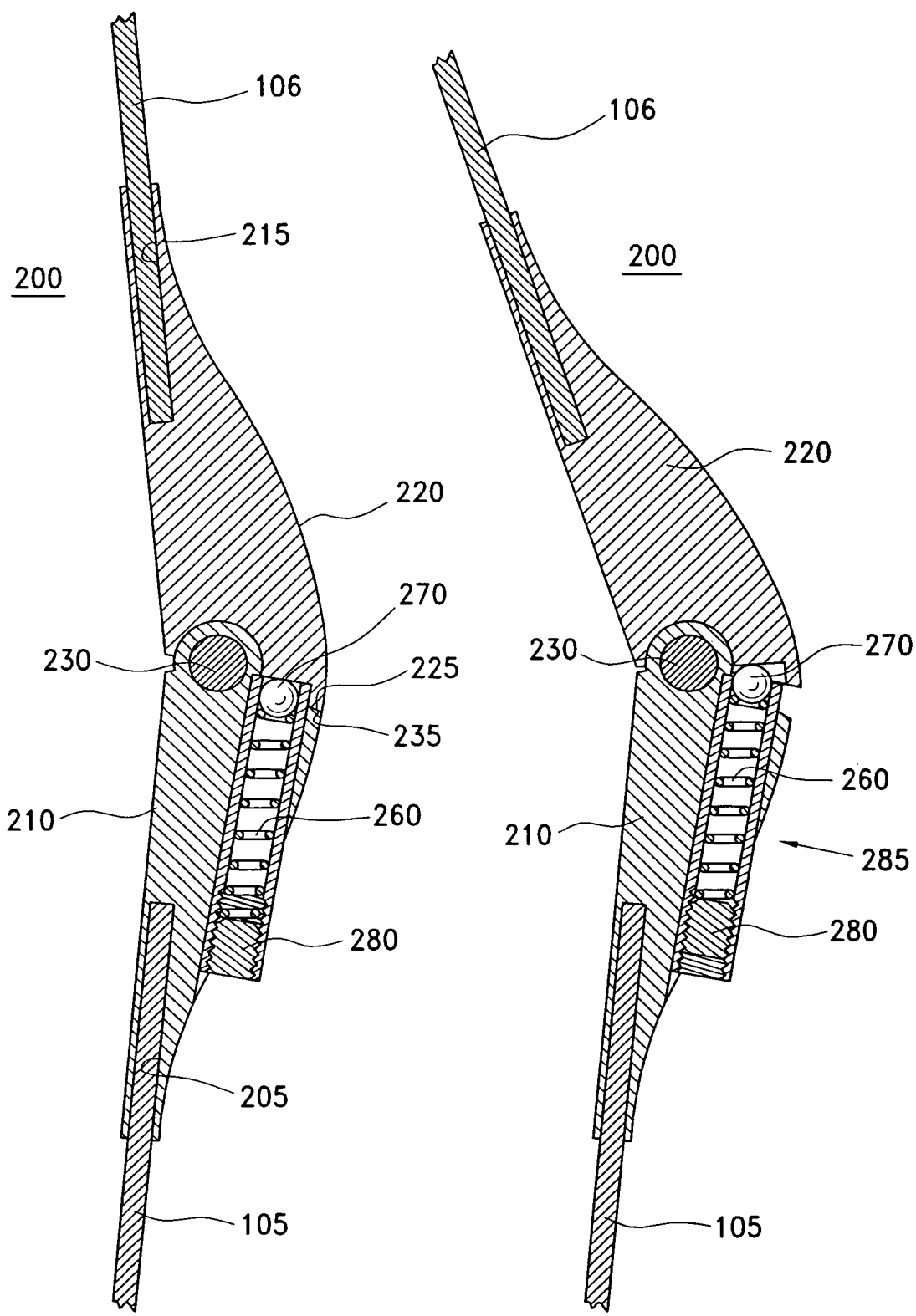
FIG. 3 illustrates a cross-section of the spring biased hinge in an unbiased position.
FIG. 4 illustrates a cross-section of the spring biased hinge in a biased position.

As illustrated in greater detail in FIG. 3, the spring biased hinge 200 is illustrated in a closed position. In the closed position, the spring biased hinge is held in a substantially linear orientation by means of bump stops 225 and 235. It should be appreciated that the thickness of the bump stops 225 and 235 can be modified such that, for example, the spring biased hinge, when closed, can be substantially linear, or, for example, adjusted such that the sternal plate 102 is angled slightly toward or away from the patient as appropriate.

As illustrated in FIG. 4, the tension adjusting mechanism 280 has been "tightened" such as to create a greater compressive force on the spring 260 thereby forcing the ball bearing 270 to press against a surface of the sternal pressure bar portion 220 thereby creating the posteriorly directed force. The tightening, in turn, presses the sternal plate against the chest of a patient. As the tension adjusting mechanism 280 is further screwed into the receiving portion 285, the posteriorly directed force increases.

As illustrated in the figures, while a coil spring is used is to create the posteriorly directed force, it should be appreciated that other spring mechanisms, such as a flat spring, or the like, could be used with equal success. Furthermore, a "mousetrap" type spring arrangement could be utilized, for example, wherein the coil portion of the mouse trap type spring surrounds the hinge pin 230. The spring could then be tensioned by a tensioning mechanism (not shown) that, for example, adjusts a non-helix portion of the spring, thus increasing the posteriorly directed force in a similar manner.

The spring tension adjusting mechanism is not be limited to the spring and tensioning adjusting screw as shown, but could also include, for example, a pneumatic or hydraulically based system, with, for example, an exterior pump that allows for the posteriorly directed force to be adjusted. More particularly, a cylinder and piston type arrangement could be used in place of the tension adjusting mechanism spring and ball bearing whereby a material, such as a fluid is injected into the cylinder which thereby extends a piston that presses against the surface of the sternal pressure bar 230 and increases the posteriorly directed force.

It should further be appreciated that the bias mechanism can be interchanged based on, for example, the intended patient use. For example, for use with a child, the spring 260 could be switched for a spring with lesser bias. Alternatively, for example, for a large patient, a larger spring could be used to provide more substantial posteriorly directed force.

FIGS. 5 and 6 illustrate environmental views of the orthosis module 100. In particular, FIG. 5 illustrates the orthosis module 100 where the sternal plate 102 is resting against the patient's chest and the spring biased hinge 200 is in the closed position. FIG. 6 illustrates the orthosis module 100 with the spring biased hinge 200 providing a posteriorly directed force which is thereby pressing the sternal plate 102 against the chest of the patient thereby keeping the patient in a more erect position.

It is, therefore, apparent that there is provided, in accordance with the present invention, an orthosis system. While this invention has been described in conjunction with a number of embodiments, many alternatives, modifications, and variations would be apparent to those of ordinary skill in the applicable arts. Accordingly, all alternatives, modifications, equivalents and variations are intended to be included within the spirit and scope of this invention.

The invention claimed is:

1. A spinal orthosis comprising:

a torso unit;

a base member secured to the torso unit;

a spring biased hinge having a center of rotation and being connected at a first end to the base member and connected at a second end to a sternal support, the spring biased hinge having a horizontal articulation and an anterior-posterior range of movement;

one or more sternal pads connected to the sternal support, the sternal pads adapted to provide a posteriorly directed force based on a bias of the spring biased hinge, wherein the spring biased hinge includes at least one bump stop that limits the range of movement of the spring biased hinge and a receiving portion at least partially integrated in the spring biased hinge, said receiving portion including a first end and a second end and housing an adjustment mechanism at the first end and a spring to provide the bias for the spring biased hinge, wherein the adjustment mechanism is moveable through the receiving portion to adjust the bias provided for the spring biased hinge, the adjustment mechanism being movable toward the second end of the receiving portion to increase the posteriorly directed force and being movable away from the second end of the receiving portion to decrease the posteriorly directed force, wherein a force line associated with the bias of the spring is arranged at an angle with respect to the center of rotation of the spring biased hinge, and wherein the spring provides bias for the spring biased hinge at a position along the force line that is substantially directly anterior to the center of rotation, with anterior being defined with respect to the range of movement of the spring biased hinge.

2. The spinal orthosis according to claim 1, wherein the receiving portion further houses a ball bearing at the second end of the receiving portion; and the spring is positioned in the receiving portion between the adjustment mechanism and the ball bearing.

3. The spinal orthosis according to claim 1, wherein one bump stop of the at least one bump stop is configured to be moveable with respect to the receiving portion, and wherein said one bump stop of the at least one bump stop is configured to overlap the second end of the receiving portion.

4. The spinal orthosis according to claim 1, wherein the spring biased hinge includes a built-in cant based on the at least one bump stop.

5. An orthosis module comprising:

a torso support; and a sternal plate connected, via a spring biased hinge, to the torso support, the spring biased hinge having an axis of rotation and being adapted to cause the sternal plate to provide a posteriorly directed force;

wherein the spring biased hinge has a horizontal articulation and an anterior-posterior range of movement and includes:

a coil spring having a posterior-superior axis and adapted to bias the spring biased hinge; and a mechanism that moves relative to the spring along the spring's posterior-superior axis to alter the posteriorly directed force, wherein the mechanism is provided so as to be canted with respect to the axis of rotation of the spring biased hinge.

6. The module of claim 5, wherein the mechanism is a tension adjusting mechanism.

7. The module of claim 5, further comprising one or more adjustable straps.

8. The module of claim 5, wherein a sternal pressure base connects the spring biased hinge and the torso support.

9. The module of claim 5, wherein a sternal pressure support connects the spring biased hinge and the sternal plate.

10. The module of claim 5, wherein the sternal plate includes one or more pads.

11. The module of claim 5, wherein the spring biased hinge further includes:
bump stops that limit the operation of the spring biased hinge;
a bar portion; and
a base portion,
wherein the bar portion is coupled to the sternal plate,
wherein the base portion is coupled to the torso unit,
wherein a first bump stop is formed in one piece with the bar portion and a second bump stop is formed in one piece with the base portion, and
wherein the first bump stop is configured to be substantially flush with the second bump stop at a maximum open angle of the spring biased hinge.

12. The orthosis according to claim 5, wherein the mechanism and the coil spring are housed in a receiving portion partially integrated into the spring biased hinge, with a portion of the receiving portion being exposed from the spring biased hinge.

13. A spinal orthosis comprising:
a torso unit;
a base member secured to the torso unit;
a biased hinge having an axis of rotation and including a bar portion and a base portion, the base portion being secured to the base member, and the bar portion being secured to a sternal support;
a sternal plate with at least one pad connected by the sternal support to the biased hinge, the sternal pad providing a posteriorly directed force based on a bias of the biased hinge,
wherein the biased hinge further includes a mechanism that alters the posteriorly directed force by adjusting a pressure applied directly to a surface of the bar portion, and
wherein the mechanism is provided so as to be canted with respect to the axis of rotation of the biased hinge.

14. The spinal orthosis of claim 13, wherein the mechanism comprises a piston.

15. The spinal orthosis of claim 14, further comprising a cylinder in which a fluid pressure can be increased to increase the posteriorly directed force.

16. The module of claim 13, wherein the mechanism comprises at least one of a coil spring, a pneumatic system, and a hydraulic system.

17. The spinal orthosis of claim 13, wherein the mechanism comprises a coil spring.

18. The spinal orthosis according to claim 13,
wherein the biased hinge further includes a receiving portion integrated therein, said receiving portion being partially exposed from the biased hinge, housing at least a portion of the mechanism, and having a first end and a second end; and the mechanism is moved toward the second end of the receiving portion to increase the posteriorly directed force and is moved away from the second end of the receiving portion to decrease the posteriorly directed force.

19. The spinal orthosis according to claim 13,
wherein, at all times, the bar portion and the base portion are positioned at a preset, non-zero angle with respect to each other, and
wherein a force line associated with the bias of the biased hinge is arranged to act anterior to the axis of rotation so as to force the bar portion posteriorly, with anterior being defined with respect to a range of movement of the spring biased hinge.

20. The orthosis according to claim 5, wherein the spring biased hinge includes a built-in cant based on a bump stop set.

21. The spinal orthosis according to claim 13, the biased hinge includes a built-in cant based on a bump stop arrangement.

22. The spinal orthosis according to claim 13, wherein the biased hinge further includes bump stops that limit the range of movement of the biased hinge,
wherein a first bump stop of the bump stops is formed in one piece with the bar portion and a second bump stop of the bump stops is formed in one piece with the base portion,
wherein the surface of the bar portion having a pressure applied directly thereto is recessed with respect to the first bump stop, and
wherein the first bump stop is configured to be moveable with respect to the second bump stop about the axis of rotation of the biased hinge, the first bump stop being arranged at a position on an outside of the mechanism when the biased hinge is at a maximum open angle.

23. An orthosis method comprising:
securing an orthosis module to a user, the orthosis module having a torso support, and a sternal plate connected, via a spring biased hinge, to the torso support; and
adjusting a mechanism of the spring biased hinge relative to a spring that biases the spring biased hinge to alter a posteriorly directed force provided by the sternal plate,
wherein the spring biased hinge has a horizontal articulation and an anterior-posterior range of movement and is positioned adjacent to a user's chest,
wherein a force line associated with the bias of the spring is canted with respect to a center of rotation of the spring biased hinge, and
wherein the spring provides bias for the spring biased hinge at a position along the force line that is directly anterior to the center of rotation, with anterior being defined with respect to an anterior-posterior range of movement of the spring biased hinge.

24. The method of claim 23 further comprising selecting the spring for the hinge based on the size of the patient.

25. The method according to claim 23,
wherein the spring biased hinge further includes a receiving portion integrated therein, said receiving portion being partially exposed from the spring biased hinge, having a first end and a second end, and housing the adjustment mechanism, the spring, and a ball bearing; and
the adjustment mechanism is positioned at the first end of the receiving portion and the ball bearing is positioned at the second end of the receiving portion.

* * * * *